United States Patent [19]

Suzuki

[11] Patent Number: Plant 7,138

[45] Date of Patent: Feb. 6, 1990

[54] ROSE PLANT — KEIROMO VARIETY

[75] Inventor: Seizo Suzuki, Tokyo, Japan

[73] Assignee: The Conard-Pyle Company, West Grove, Pa.

[21] Appl. No.: 299,679

[22] Filed: Jan. 23, 1989

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which abundantly forms elegant long lasting double blossoms which are scarlet pink on the inside and light carmine rose on the outside. The buds are large and of good form. The plant exhibits vigorous vegetation and is well suited for forcing and cut flower production. The plant forms dense and glossy foliage and is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Jofitali variety (U.S. Plant Pat. No. 4,083). The male parent (i.e., the pollen parent) was the Happiness variety (U.S. Plant Pat. No. 911). The parentage of the new variety can be summarized as follows:

Jofitali × Happiness.

The seeds resulting from the above pollination were sown in a greenhouse and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance elegant long lasting blossoms which are scarlet pink on the inside and light carmine rose on the outside,
(b) is well adapted for forcing,
(c) exhibits vigorous glossy vegetation, and
(d) is particularly suited for cut flower production.

The buds are large and of good form.

The new variety well meets the needs of the cut flower industry since the blossoms are highly attractive and are formed in abundance. It also is suited for other horticultural uses.

The new variety has been found to undergo asexual propagation by a number of routes, including budding, grafting, cuttage, etc. The characteristics of the new variety have been found to be strictly transmissable by such asexual propagation from one generation to another.

The new variety has been named the Keiromo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while grafted on *Rosa indicia* and growing in a greenhouse at Cap d'Antibes, France.

DETAILED DESCRIPTION

Figures 1, 2, 3, 4, 5, 6, 7, 8, 9, 10, 11, 12, 13, 14, 15, 16:
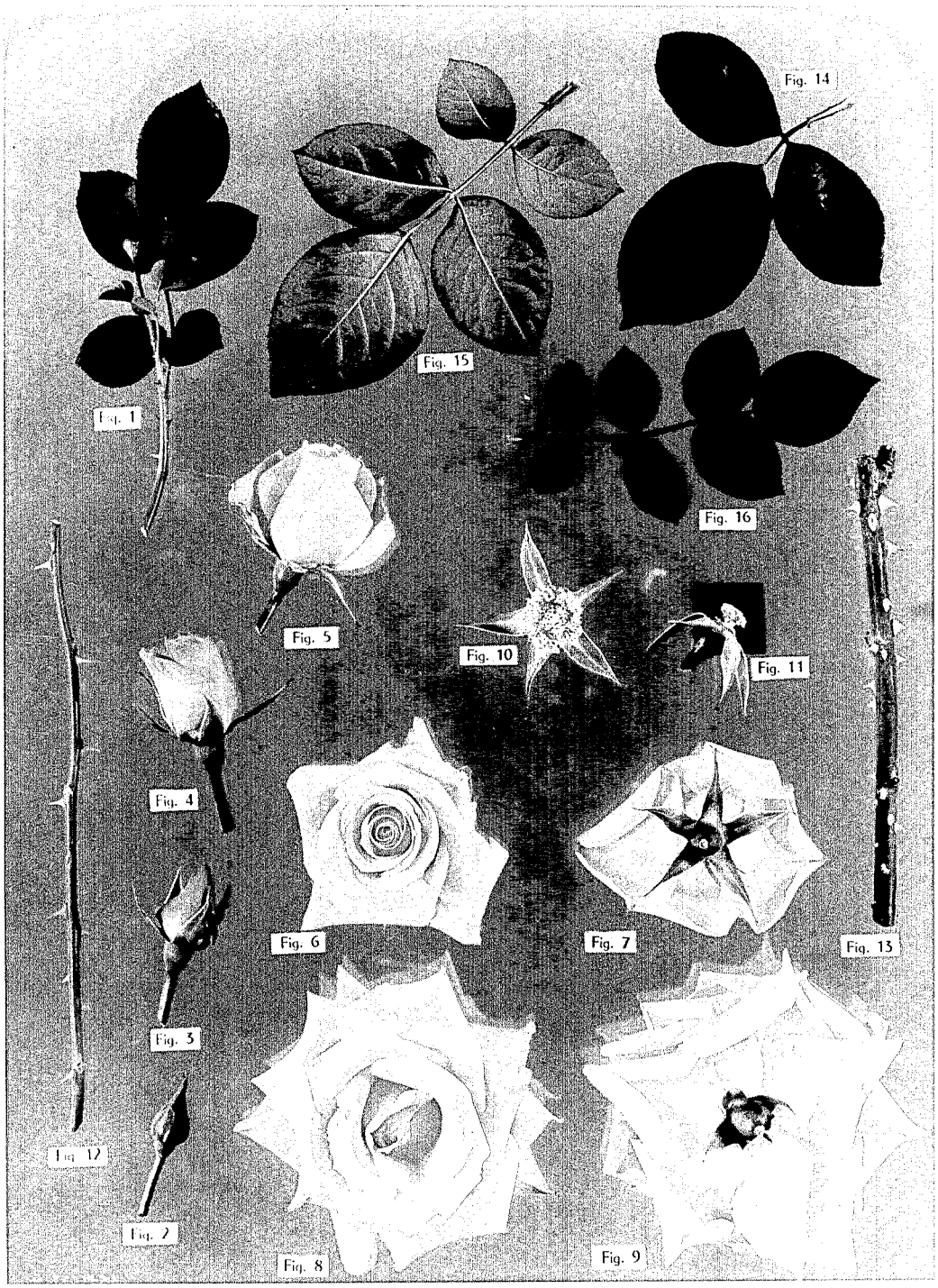
FIG. 1 illustrates a specimen of a young shoot with bud.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on two year old plants made during February while grafted on *Rosa indicia* understock and growing in a greenhouse at Cap d'Antibes, France. The coloration in common terms precedes reference to the chart.

Class: Hybrid Tea.

Plant:

*Height.*—Plants where were pruned to a height of 85 cm. produce floral stems having a length of approximately 50 to 70 cm.

*Habit.*—Upright.

Branches:

*Color.*—Young stems: light green, Green Group 143A, more or less shaded with reddish brown. Adult wood: medium green, Green Group 137B.

*Thorns.*—Size: average. Quantity: average. Color: greenish in coloration on young stem and light brown on mature wood.

Leaves:

*Stipules.*—Adnate, pectinate, somewhat wide and linear.

*Petioles.*—Upper surface: striped, reddish brown on young leaves and medium green with glandular edges on adult foliage. Under surface: light green, bear a few thorns.

*Leaflets.*—Number: 3, 5, and 7 (most often). Shape: oval. Serration: simple and regular. Texture: consistent. General appearance: dense bright foliage. Color (young foliage): upper surface: medium green, Green Group 137A. under surface: light green, Green Group 137C, and widely tinted with reddish brown. Color (adult foliage): upper surface: dark green, Green Group 139A. under surface: light green, Green Group 137C.

Inflorescence:

*Number of flowers.*—Generally one per stem.

*Peduncle.*—Upright, rigid, light green in coloration, and bears numerous glandular prickles. The length is approximately 11 to 12 cm. on average.

*Sepals.*—Upper surface: tomentose, greenish in coloration. Under surface: light green in coloration, the edges of the outer sepals are glandular and slightly appendiculated.

Buds.—Shape: conical. Length: approximately 4.5 cm. on average. Size: large. Color upon opening: upper surface: scarlet pink, Red Group 43C, and lighter at the edges of the petals. under surface: claret rose, Red Group 50B, and lighter at the edges of the petals.

*Flower.*—Shape: initially elongated, changing to cuplike with a conelike center. Diameter: approximately 12 to 13 cm. on average. Color (when opening begins): upper surface: dark scarlet pink, Red Group 43D. under surface: carmine rose, Red Group 52C. Color (when blooming): upper surface: dark scarlet pink, Red Group 43D with lighter edges. under surface: light carmine rose, Red Group 52D. Color (at end of opening): upper surface: scarlet pink, Red Group 43D. under surface: light carmine rose, Red Group 52D. Fragrance: none. Lasting quality: long. Petal number: approximately 32 on average plus 3 to 4 petaloids commonly are present. Texture: consistent. Petal drop: fairly good. Stamen number: approximately 234 on average. Anthers: normal, yellowish in coloration. Filaments: free-standing, bright yellow with fuchine tips, of irregular heights. Pistils: approximately 172 on average. Stigmas: normal, straw colored, located below the stamens. Styles: free-standing, light fuchsine in coloration, of irregular heights. Receptacle: light green, in longitudinal section are in the shape of a wide pitcher.

Development:

*Vegetation.*—Vigorous.

*Blooming.*—Quite abundant.

*Resistance to diseases.*—Good.

*Aptitude to forcing.*—Excellent.

I claim:

1. A new and distinct variety of Hybrid Tea rose plant characterized by the following combination of characteristics:

(a) forms in abundance elegant long lasting blossoms which are scarlet pink on the inside and light carmine rose on the outside, (b) is well adapted for forcing, (c) exhibits vigorous glossy vegetation, and (d) is particularly suited for cut flower production;

substantially as herein shown and described.

* * * * *